United States Patent [19]

Urdal et al.

[11] Patent Number: 4,658,018

[45] Date of Patent: Apr. 14, 1987

[54] PROCESS FOR PRODUCING HOMOGENEOUS COLONY STIMULATING FACTOR

[75] Inventors: David L. Urdal; Carl J. March; Diane Y. Mochizuki; Paul J. Conlon, III, all of Seattle, Wash.

[73] Assignee: Immunex Corporation, Seattle, Wash.

[21] Appl. No.: 588,940

[22] Filed: Mar. 13, 1984

[51] Int. Cl.$^4$ .......................... C07K 3/20; C12P 21/00
[52] U.S. Cl. ..................................... 530/351; 530/417; 435/68
[58] Field of Search ...................... 435/68; 260/112 R; 424/85, 88; 530/351, 417

[56] References Cited

U.S. PATENT DOCUMENTS 4,504,586  3/1985  Nicolson ............................... 435/68

OTHER PUBLICATIONS

Chemical Abstracts, vol. 100, Abstract Nos. 101380n and 45417, 1984.
Chemical Abstracts, vol. 97, Abstract Nos. 175204z, 1981 and 70635n, 1982.
Chemical Abstracts, vol. 94, Abstract No. 42884n, 1981.
Chemical Abstracts, vol. 91, Abstract Nos. 121029d and 103981d, 1979.
Chemical Abstracts, vol. 89, Abstract No. 102287d, 1978.
Ihle et al., *J. Immun.*, 126: 2184 (1981).
Ihle et al., *J. Immun.*, 131: 282 (1983).
Ihle et al., *J. Immun.*, 129: 2431 (1982).
Fung et al., *Nature*, 307: 233 (1984).
Yokota et al., *Proc. Natl. Acad. Aci. USA*, 81: 1070 (1984).
Burgess et al., "Granulocyte/Macrophage-, Megakaryocyte-, Eosinophil—and Erythroid—Colony-Stimulating Factors Produced by Mouse Spleen Cells," 185, *Biochem. J.*, 301 (1980).
Bazill et al., "Characterization and Partial Purification of Haemopoietic Cell Growth Factor in WEHI-3 Cell Conditioned Medium," 210, *Biochem. J.*, 747 (1983).
Dexter et al., "Growth of Factor-Dependent Hemopoietic Precursor Cell Lines," 152, *J. Exp. Med.*, 1036 (1900).
Clark-Lewis and Schrader, "Biochemical Characterization of Regulatory Factors Derived from T-Cell Hybr. and Spleen Cells," 128, *J. of Immunology*, (1982), pp. 168–174.
Horiuchi and Ichikawa, "Control of Macrophage and Granulocyte Colony Formation by Two Different Factors," 110, *Exp. Cell Res.*, 79 (1977).
D. Metcalf, "Production of Colony Stimulating Factors by Lymphoid Tissues," *Biol. of the Lymphokines*, (1979), pp. 515–540.
Parker and Metcalf, "Production of Colony-Stimulating Factor in Mitogen-Stimulated Lymphocyte Cultures," 112, *J. of Immunology*, 502 (1974).
N. Williams et al., "Differentiation of Mouse Bone Marrow Precursor Cells into Neutrophil Granulocytes by an Activity Separation from WEHI-3 Cell-Conditioned Medium," *Differentiation*, pp. 59–63 (1978).

*Primary Examiner*—Blondel Hazel

[57] ABSTRACT

Colony stimulating factor derived from malignant cells has been purified by use of various techniques including multiple high performance liquid chromotography steps. By this technique, colony stimulating factor has been resolved into distinct species, and one of the species denominated as CSF-2A, has been purified to homogeneity. The high purification of the CSF-2A has enabled the amino acid composition of this protein molecule to be partially sequenced with an automated sequencer.

4 Claims, 1 Drawing Figure

PROCESS FOR PRODUCING HOMOGENEOUS COLONY STIMULATING FACTOR

TECHNICAL FIELD

The present invention relates to homogenous colony stimulating factor, and more particularly to purified granulocyte-macrophage colony stimulating factor derived from malignant cells and a process for producing same.

BACKGROUND OF THE INVENTION

Colony stimulating factor refers to a family of lumphokines which induce progenitor cells found in the bone marrow, to differentiate into different types of mature blood cells. The particular type of mature blood cell that results from a progenitor cell depends on the type of colony stimulating factor present. For instance, erythropoietin causes progenitor cells to mature into erythrocytes while thrombopoietin is thought to drive progenitor cells along the thrombocytic pathway. Similarly, granulocyte-macrophage colony formation is dependent on the presence of a granulocyte-macrophage colony stimulating factor (hereinafter referred to as "CSF"). The present invention concerns the production of CSF from malignant cells, the resolution of CSF into distinct species, and the purification of one of the species (CSF-2α) to homogeneity.

Researchers have reported the detection and production of CSF from a variety of different sources. CSF has been detected in serum and urine. Robinson et al., 69 *J. Cell. Physiol.* 83–92 (1967); Stanley et al., 79 *J. Lab. Clin. Med.* 657–668 (1972). CSF also has been extracted from substantially all of the organs of the body. Sheridan and Stanley, 78 *J. Cell. Physiol.* 451–459 (1971). Several researchers have reported the production of CSF from both human and monkey peripheral blood cells which appear to be macrophages or monocytes. Moore and Williams, 80 *J. Cell. Physiol.* 195–206 (1972); Golde and Kline, 51 *J. Clin. Invest.* 2981–2983 (1972); Moore et al., 50 *J. Natl. Cancer Inst.* 591–601 (1973). In the past, CSF also has been produced by T and B cells stimulated with serum and an appropriate plant mitogen. Parker and Metcalf, 112 *J. Immunol.* 502–510 (1974). CSF also has been produced by culturing T-cell hybridomas in the presence of a T-cell mitogen. Clark-Lewis and Schrader, 128 *J. Immunol.* 168–174 (1982).

Although the factors identified by the above researchers have been reported to be CSF, heretofore CSF has not been purified to homogeneity. As a result, relatively little is known about the specific functions and activities of the various subspecies of CSF.

Burgess et al., 185 *Bilochem. J.* 301–314 (1980), discussed the simultaneous production of granulocyte/-macrophage (CSF), eosinophil, megakarocyte and erythroid regulatory factors by activating murine spleen cells with pokeweed mitogen in the presence of human serum. Burgess et al. reported "partial purification" of these factors by a procedure involving ammonium sulfate precipitation/dialysis, gel filtration chromatography (Sephadex G-500), ionic exchange chromatography (DEAE cellulose), concanavalin A sepharose chromatography, flat bed gel isoelectric focusing, hydrophobic chromatography (phenyl-Sepharose). No appreciable separation of the factors thus achieved by gel filtration, concanavalin A sepharose chromatography or ammonium sulfate precipitation. Although, partial purification was achieved by isoelectric focusing, none of the CSF species, so separated could be shown to be homogeneous.

Williams et al., 11 *Differentiation* 59–63 (1978), reported the deriving of colony stimulating activities from a conditioned medium of a myelomonocyte leukemic cell line designated as WEHI-3. The WEHI-3 conditioned medium was found to stimulate formation of granulocyte, macrophage and megakaryocyte colonies. However, when the WEHI-3 condition medium was subjected to DEAE-Sephadex A-25 column chromatography, it appeared that separate activities were fractionated, one stimulating macrophage colony formation while the other stimulating granulocyte colony formation, suggesting that granulocyte and macrophage development may be dependent upon separate regulators. See also, Horiuchi and Ichikawa, 110 *Exp. Cell Res.* 79 (1977).

Clark-Lewis and Schrader, supra, reported the production of CSF, T-cell growth factor (TCGF) (also known as interleukin-2) and T-cell replacing factor (TFR) from a T-cell hybridoma stimulated with concanavalin-A. Techniques used for fractionating and purifying the three factors included ammonium sulfate precipitation, gel filtration, heat treatment and hydrophobic chromatography. The factors could not be separated from each other by ammonium sulfate precipitation. The CSF product was found to have a molecular weight of from 25,000 to 30,000 by gel filtration in phosphatebuffered saline (PBS) and of about 23,000 by gel filtration in guanidine hydrochloride.

Accordingly, the principal objects of the present invention are to identify cell lines and clones thereof which are potent producers of CSF and to purify the CSF to homogenity thereby to resolve CSF into identifiable, distinct species.

Another object of the present invention is to purify crude preparations of CSF to homogeneity by reverse phase, high performance liquid chromatography techniques.

A further object of the present invention is to ascertain, at least in part, the amino acid sequence of CSF.

BRIEF DESCRIPTION OF THE DRAWINGS

The details of a typical embodiment of the present invention will be described in connection with the accompanying drawing, in which.

DETAILED DESCRIPTION OF THE INVENTION

Figure 1:
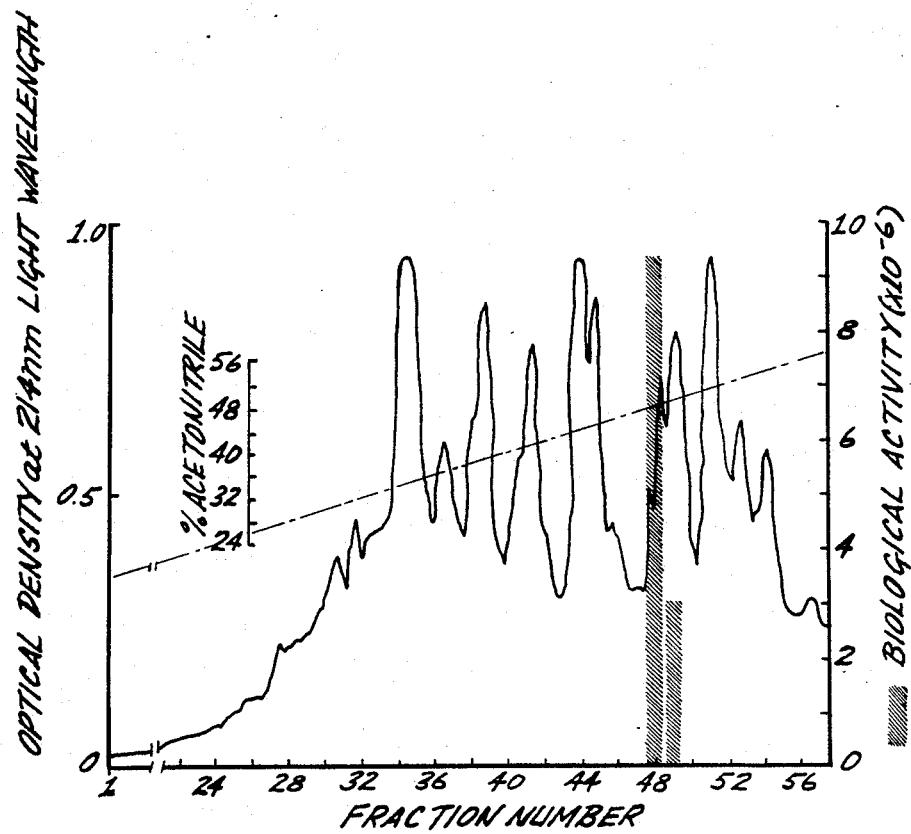
FIG. 1 illustrates the results of reverse phase high-performance liquid chromatography purification process in which the CSF was eluted from the column with an acetonitrile gradient. The hatched line indicates biological activity in Units as measured with FDC-P2 assay.

The present invention relates to the production of CSF from malignant cells, to the purification of the CSF into homogeneous subspecies, and to the determination of the amino acid sequence of the amino terminal portion of one of these species. The CSF of the present invention has the capacity to stimulate the growth of granulocyte andmacrophage colonies from individual bone marrow cells in agar cultures in vitro and the capacity to promote the differentiation and proliferation of bone marrow cells in vitro into mature granulocytes and macrophages. The procedure of the present invention utilized to produce the CSF includes culturing malignant cells in vitro in a medium supplemented with various additives and stimulated with a T-cell mitogen. The CSF is resolved into distinct species by various chromatography techniques. One of these species, designated as CSF-2α, is purified to homogeneity by reverse phase, high performance liquid chromatography (HPLC).

Crude preparations of CSF are prepared by initially culturing malignant neoplastic cells in vitro in a serum containing medium supplemented with various additives. After a suitable culture period, the cells are harvested and then resuspended in an appropriate serumless medium in the presence of a T-cell mitogen, such as phytohemaggelutinin (PHA), thereby producing a supernate which contains CSF. After a period of time, the supernate is collected and processed to purify the CSF into a more concentrated form.

Cell lines which can be employed in the production of crude CSF include various T and macrophage cell lines, as well as various T-lymphoma cell lines. The cell lines were produced by either spontaneous occurrence, via viral transformation or via transformation by chemical carcinogen or irridation. The above process has been used in conjunction with a radiation-induced splenic lymphoma cell line from the B10.BR mouse, designated as LBRM-33. This cell line is available from a wide variety of commercial and private sources and has been used extensively by U.S. and foreign researchers. The purification process of the present invention can also be used to purify CSF from sources other than B and macrophage cell lines, such as from body fluids and organs and from peripheral blood cells.

The culture media used to produce crude CSF, in conjunction with the aforesaid cell lines, may consist of commercially available media, such as Roswell Park Memorial Institute ("RPMI") medium, Delbecco Modified Eagle Medium ("DMEM") and Click's Medium. Additives, which may be individually or in combination, added to the culture medium include penicillin, streptomycin, gentamycin, fresh L-glutamine, N-2-hydroxy-piperazine-XI$^1$-2-ethylene-sulfonic acid ("HEPES") buffer, $NaHCO_3$, 2-mercaptoethanol, fetal calf serum (FCS) or normal human serum.

The initial cell density of cells, particularly when LBRM-33 cells are employed, should be in the range of about $1 \times 10^5$ cells/ml to $3 \times 10^6$ cells/ml, and most preferably about $1 \times 10^5$ cells/ml for the initial cell culture and about $1-2 \times 10^6$ cells/ml for the subsequent mitogen stimulated culture. Cell densities above or below this range may result in lower yields of CSF per number of initial cells.

In the CSF production process of the present invention, several different stimulating mitogens may be utilized. These mitogens include different plant glycol proteins, such as concanavalin A (Con A), PHA and pokeweed mitogen (PKM). Applicants have found that the specific concentrations of the particular mitogen used affects the amount of CSF produced. For optimal initial cell concentrations of, for instance, LBRM-33 cells, an optimal concentration of Con A is approximately 20–50 μg/ml. Correspondingly, optimal amounts of PHA mitogen is in the range of 0.5% to 2.0% by volume, and preferably approximately 1% by volume. It is to be understood that if different concentrations of LBRM-33 cells are employed, or if another cell line is used, the concentrations of Con A and PHA may have to be adjusted to obtain maximum CSF production.

The present process for producing CSF from malignant cell lines may be carried out in various environmental conditions. Preferably, however, the cultures should be maintained in the temperature range of approximately 35°–38° C. in a humidified atmosphere of from approximately 5–10% carbon dioxide in air. Also, ideally the pH of the culture medium should be kept in slightly alkaline condition, in the range of approximately pH 7.0–7.4.

The quantity of CSF produced by stimulating malignant cells with a plant mitogen varies with time. Peak levels of CSF are reached at approximately 16–24 hours after stimulation by PHA.

The present invention also includes identifying potent cell line sources of CSF by cloning cell lines known to produce significant quantities of CSF. Thereafter, the cloned cell lines are cultured in a medium which may be supplemented with various additives and stimulated with a plant mitogen in the same manner in which CSF is produced from LBRM-33 lymphoma cells, as outlined above. Cloning is accomplished by a limiting dilution procedure wherein cells from selected cell lines, such as LBRM-33, are cultured in flat-bottom microplate wells. The cells are seeded in 200 microliter volumes of RPMI-1640 supplemented with FCS at cell density of 0.5 cells per milliliter. After approximately 10 days, the microplate wells which house viable cell growth are harvested and then subcultured in tissue flasks containing a medium composed of RPMI-1640 supplemented with FCS. A plant mitogen, such as PHA or Con A, is used to stimulate viable cell CSF production. Once the subcloned cultures have reached a density of approximately $10^6$ cells per ml, cultures are harvested and tested for CSF production. One particular subclone, designated as LBRM-33-5A4, was found to produce significant quantities of CSF.

Assays for CSF are employed to monitor the cell culture production procedure and to monitor the purification procedures used in conjunction with the present invention. One preferred assay involves ascertaining the capacity of the sample to induce proliferation of the factor dependent murine cell line FDC-P2, derived from mouse bone marrow (hereinafter "FDC-P2 assay"). Briefly, the FDC-P2 assay includes seeding from approximately $10^3$ to $10^4$ FDC-P2 cells in 100 microliter volumes in a $\log_2$ dilution series of potential CSF containing samples. The mixture is cultured for twenty-four hours at 37° C. in a humidified atmosphere of 5% $CO_2$ in air. The cultures are then pulsed for approximately 4 hours with 0.5 microcuries of tritiated thymidine ($^3$H-Tdr, New England Nuclear, Boston Mass., 20 Ci/mM specific activity) after which the cultures were harvested onto glass fiber filter strips, for instance with the aid of a multiple, automated sample harvester. $^3$H-Tdr incorporation is then measured by liquid scintillation counting.

By this procedure, only the FDC-P2 cells cultured in the presence of CSF were found to incorporate $^3$H-Tdr in a dose dependent manner. FDC-P2 cells cultured in the absence of CSF incorporated only background levels of $^3$H-Tdr. Units of CSF activity were determined as the reciprocal dilution of a sample which generated 50% of maximal FDC-P2 $^3$H-Tdr incorporation as compared to a laboratory standard (WEHI-3b macrophage cell line conditioned medium). For example, if a sample generated 50% of maximal FDC-P2 $^3$H-Tdr incorporation at a dilution of 1:10, 1/10 of 100 μl (assay volume) or 10 μl was said to contain 1 unit. The sample would therefore contain 100 units (1000÷10) of CSF activity/ml. Additional details of the assay procedure are set forth in Dexter et al., 152 *J. Exp. Med.* 1036–1047 (1980); Brazil et al., 120 Biochem. J. 747–759 (1983).

A second assay employed in conjunction with the present invention involves ascertaining the capacity of CSF samples to induce proliferation of bone marrow cells obtained from the femurs and tibias of BALB/C or (BALB/C×DBA/2) F1 mice (4–8 weeks old). The cells are suspended in RPMI-1640 medium containing either 5% or 10% FCS by volume, 50 units/ml penicillin, 50 μg/ml streptomycin, 2 mM L-glugamine and $5\times10^{-5}$M 2-mercaptoethanol at a density of $5\times10^5$ cells per ml. This suspension is placed in flat-bottom 96-well microliter plates (200 μl) and then the fractions to be assayed (20 μl or less) are added to each well. After 72 hours at 37° C. in a humidified atmosphere of 5% $CO_2$ in air, 0.5 uC of $^3$H-Tdr (2-20 Ci/mM, New England Nuclear, Boston, Mass.) are added to each well. The cultures are harvested onto glass fiber filter strips after a further 16 hour incubation. $^3$H-Tdr incorporation is then measured by liquid scintillation counting.

Only the bone marrow cells cultured in the presence of CSF were found in incorporate tertiated $^3$H-Tdr in a dose dependent manner. Bone marrow cells cultured in the absence of CSF incorporated only background levels of $^3$H-Tdr. Units of CSF activity were determined in the same manner as in the FDC-P2 assay above.

The CSF produced by the above procedure is initially concentrated by ammonium sulfate precipitation. Cell-free supernate is filtered to remove debris. Thereafter, ammonium sulfate is added in stepwise manner to 30%, 50% and finally to 80% saturation. Addition of ammonium sulfate for precipitation is done over an extended period of time. The precipitate obtained is pelleted by centrifugation and the pellet resuspended in 10mM Tris buffer (pH 8.0). This solution is dialyzed against 10mM Tris buffer (pH 8.0).

The dialyzed concentrate obtained from the ammonium sulfate precipitation is subjected to ion-exchange chromatography. A suitable column material for this purpose is diethyl amino ethyl (DEAE) Sephacel. The DEAESephacel column is equilibrated with an appropriate buffer and the sample concentrate applied to the column. Elution is initially carried out with the starting buffer and then subsequently with a linear gradient of NaCl (0-1000 mM) in the same buffer. Fractions are collected, sterilized and then assayed for CSF activity using the procedure previously discussed.

Bone marrow assay of the ion-exchange chromatography results have revealed a first major peak of CSF activity which does not bind to the DEAE column equilibrated in 10mM Tris buffer, pH 8.0. This activity has been denominated as CSF-2α. Additional activity peaks have been eluted as various concentrations of the NaCl. The CSF-2α activity was verified by use of the FDC-P2 assay, discussed above.

The fractions containing CSF-2α from the DEAE Sephacel chromatography procedure are pooled to provide a starting material for the HPLC procedures. However, if the pooled fractions contain too much protein (20–120 mg), the fractions are subjected to a cation exchange column chromatography process prior to employing HPLC. A suitable column for this purpose is composed of sulfylpropyl (SP) Sephadex (Pharmacia Fine Chemicals, Piscataway, N.J). Preferably the column is equilabrated with an appropriate buffer prior to application of the CSF-2α sample and then washed with the same buffer after the CSF-2α sample has been applied to the column. Elution is carried out with a linear salt gradient in the same buffer. Fractions are collected, sterilized and assayed as above.

The pooled active fractions from either the above DEAE sephacel column chromatography or cation exchange column chromatography are used as a starting material for the HPLC procedures. The HPLC steps used in the present invention preferably employ a reverse phase, octadecyl bonded silica column having a pore size sufficient large to be optimally utilized with the proteineaceous CSF-2α, i.e. a pore size of at least 100 Å.

Suitable reverse phase HPLC columns for use in the practice of the present invention are articles of commerce. A preferred column for this purpose is the Porasil line of columns commercially available from Waters Assoc. Milford, Mass. For example, the present invention may employ the Waters C18 u Bondapak reverse phase column consisting of octadecyl silane groups covalently bonded by means of a siloxane (silicon-oxygen-silicon) bond to the surface of the 300 Å pore diameter silica gel which has been classified to a mean particle size of from 8 to 12 microns.

Prior to applying the CSF-2α sample to the column, the pooled CSF-2α fractions were rendered acidic by an appropriate acid. The elution of proteins from the HPLC column is carried out in a manner well known in the art. A suitable elution procedure for removing the bonded proteins from the octadecyl column involves the use of a linear gradient of acetonitrile. A preferred gradient for this purpose is 0 to 95% vol./vol. gradient in trifluoroacetic acid (TFA), pH 2.0–2.1.

The eluted protein can be conveniently monitored with detection systems that are well known in the art. For example, an automated fluorescence detection system as described by Stein and Moschera, 78 *Methods Enzymol.* 435 (1981), may be employed. Alternatively, the relative protein concentration in fractions, eluted from HPCC columns, can be determined by measuring absorbance of the eluted material in an automated ultraviolet light spectrophotometer, at 214 nanometers light wave length. A suitable automated ultraviolet light absorbance detection apparatus is available from Waters Associates, Milford, Mass.

Applicants have found that by the above reverse phase HPLC process, recovery of biologic activity is typically very good, ranging from 50 to 200% of the CSF activity applied to the HPLC column. The biological activities from the recovered fractions are tested by the above-described FDC-P2 assay. The fractions are also analyzed by polyacrylamide gel electrophoresis and silver staining, as described in Example 5 below.

If sufficient protein purification is not achieved by the initial HPLC procedure, it can be repeated by use of the same column or different type of column. In addition, the same or a different eluent may be employed. For example, in a second HPLC process, a linear gradient of N-propanol in an appropriate pyridincacetate buffer solution may be utilized.

By carrying out the HPLC process in two steps, applicants have purified CSF-2α to homogeneity as a single symmetrical peak of biological activity. Applicants have used polyacrylamide gel electrophoresis to identify a single band of CSF-2α, activity having a molecular weight of approximately 24,500 and a pI of about 5.50. The specific activity of this homogeneous CSF-2α was found to be approximately $1.1 \times 10^7$ U/ug protein, or $2.6 \; 10^{17}$ U/mole.

The ability to prepare homogeneous CSF-2α has permitted applicants to determine the amnio acid composition and sequence of the amino terminal portion of this molecule. This information may be employed to assist in the cloning of the CSF-2α gene and the ultimate production of large quantities of pure recombinant CSF-2α for clinical trials and ultimately for widespread medical use of this specific factor. Moreover, the availability of homogeneous CSF-2α will allow accurate, biological studies of its activity free from contamination by other species of CSF or other numerous lymphokine species which are known to be co-produced with CSF-2α during the induction procedure.

While the prior art has said to have achieved highly purified CSF preparations, experience has shown that when such preparations have been used as starting material in the present HPLC process, the material is resolvable into a large number of protein peaks which are unassociated with CSF-2α activity. Based on such observations, it is believed that such preparations are no more than 10% pure and in some instances may even be less than 1% pure.

Samples of homogeneous CSF-2α as prepared above can be analyzed for amino acid composition and sequence, for instance with an automated sequencer, such as with an Applied Biosystems Model 470A protein sequencer. Ideally, several sequencing runs are made to confirm the accuracy of the sequence. Through this technique, applicants have found that the first fifteen residues of the amino terminal portion of the CSF-2α molecule are composed of the following sequences: Ala-Ser-Ile-Ser-Gly-Arg-Asp-Thr-His-Arg-Lys/Leu-Thr-Arg-Thr-Leu. Residue No. 11 could not be unambiguously designated as either Lys or Leu.

The processes and products of the present invention are further illustrated by the following examples.

EXAMPLE 1

CSF Production

LBRM-33 cells in a concentration of $10^5$ cells per ml are cultured in multiple 4 liter volumes in Wheaton spinner flasks or in 150 ml volumes in replicate T175 $CM^2$ plastic culture flasks, in RPMI-1640 medium. The medium is supplemented with 10% FCS, 300 μg/ml fresh L-glutamine, $5 \times 10^{-5}$M 2-mercaptoethanol, 50 μg/ml streptomycin, 50 μg/ml penicillin and 50 μg/ml gentamycin (complete RPMI 1640 medium).

The cells are cultured from 3–5 days in a humidified atmosphere of 5% $CO_2$ in air. After this period of time viable cells are harvested by centrifugation and resuspended in complete RPMI-1640 medium, but without serum, at a concentration of $1-2 \times 10^6$ cells/ml. These cells are stimulated by the addition of 1% PHA-M (Grand Island Biological Company, Grand Island, N.Y.) or from 10 to 40 μg/ml of Con A (Calbiochem Behring, La Jolla, Calif.). Following overnight incubation at 37° C. in a humidified atmosphere of 5% $CO_2$ in air, induced cells are harvested, centrifuged and the supernates retained as a source of crude CSF-2α.

EXAMPLE 2

Cloning of CSF-Producing Cells

LBRM-33 cells are subcloned by a limiting dilution procedure in flat-bottom microplate wells. Individual LBRM-33 cells are seeded in 200 microliter volumes of RPMI-1640 supplemented with 10% by volume FCS.

After 10 days of culture, the microplate wells are screened for viable cell growth. Positive wells are harvested and then subcultured in 25 centiliter tissue culture flasks (3013 Falcon Plastics, Oxnard, Calif.) in RPMI-1640 supplemented within FCS. After the subcultures grow to a density of approximately 10×6 cells per milliliter, they are harvested and resuspended in RPMI-1640 medium supplemented with 10% by volume heat-inactivated FCS, $2.5 \times 10^{-5}$M 2-mercaptoethanol, 25 mM Hepes buffer, 50 U/ml penicillin, 50 μg/ml streptomycin, and 300 μg/ml fresh L-glutamine. The clonal subcultures are stimulated by adding PHA in a concentration of 1% by volume (PHA-M, Grand Island Biological Co., Grand Island, N.Y.) or from 10 to 40 μg/ml of Con A (Calbiochem Behring, La Jolla, Calif.).

The cultures are all maintained at approximately 37%C at a humidified atmosphere of 5% $CO_2$ in air. After 24 hours, the supernate samples from the clonal subcultures are assayed for CSF-2α activity using the procedures described above. One particular subclone, designated as LBRM-33-5A4, was found to produce especially significant quantities of CSF. The LBRM-33-5A4 cell line is on deposit with the American Type Culture Collection, 12301 Parklawn Drive, Rockville, Md. 20852, U.S.A., under deposit No. ATCC-CRL-8080.

EXAMPLE 3

Initial Purification

A. Ammonium Sulfate Precipitation 5,000–50,000 milliliters of cell-free, pooled supernatants, having an activity of approximately 3,000–10,000 units per U/ml, are filtered with a 0.45 micron filter to remove debris. Thereafter, dry ammonium sulfate is gradually added in a step-wise manner to 30%, 50% and finally to 80% saturation with gentle stirring. The ammonium sulfate is added over an extended period of time of approximately 24 hours at 4° C. Upon reaching 80% saturation, the gentle stirring is continued for an additional 8 to 24 hours in the cold. Thereafter, the mixture is centrifuged 10,000×g for 20 to 40 minutes. The resulting pellet is then dissolved in 10mM Tris buffer, pH 8.0. The solution is dialyzed against 10mM Tris buffer, pH. 8.0 for 12 to 36 hours at 4° C.

B. Ion-Exchange Chromatography

The dialyzed concentrate obtained from the ammonium precipitation is further purified by ion-exchange chromatography on a column of DEAE-Sephacel (Pharmacia Fine Chemicals, Piscataway, N.J.). The DEAE-Sephacel column is equilibrated with 10mM TRIS buffer pH 8.0 and then the sample applied to the column. Thereafter the column is initially washed with the same buffer and then elution continued with a linear gradient of 0–1000mM NaCl. Fractions are collected, sterilized and then assayed for CSF activity.

Use of the bone marrow proliferation assay revealed an initial activity peak, denominated as CSF-2α in the flow-through fraction, i.e. the peak did not bind to the DEAE column. Additional major and minor activity peaks were eluted at different concentrations of NaCl. Using the FDC-P2 assay, the CSF-2α at this stage of purification was found to have a specific activity of 100 to 500 U/μg protein.

EXAMPLE 4

Cation Exchange Chromatography

If the CSF-2α activity obtained from the DEAE Sephacel column chromatography contains too much protein, i.e. from 20 to 120 mg, the active CSF-2α containing fractions from the column are pooled, concentrated by membrane filtration (YM 10 membrane), and then dialyzed against 10 mM sodium citrate buffer (pH. 3.5) containing 100mM NaCl. The sample is then applied to SP-Sephadex C-50 cation exchange column (Pharmacia Fine Chemicals, Piscataway, N.J.) which has been previously equilibrated in the same buffer. The column is washed with the starting buffer and then with a linear gradient of NaCl (100–1000 mM) in the same buffer. Fractions are collected, sterilized and assayed as above.

By this purification protocol, applicants have found that the CSF-2 is eluted from the column at a salt concentration of 200mM NaCl. The CSF-2α at this stage exhibited a specific activity of 7000 U/μg protein.

EXAMPLE 5

Reverse Phase High Performance Liquid Chromatography With Acetonitrile Elution The active fractions obtained in Example 4 are pooled for use as a starting material for the HPLC process. The pooled fractions are rendered acidic by addition of trifluoroacetic acid (TFA) to 0.1% V/V. the acidified pool is clarified by centrifugation at 12,000 x g for 20 minutes, and then pumped directly onto a 3.9×300 mm Waters C18 u Bondapak column (Waters Assoc., Milford, Me.) at a flow rate of about 1 ml/min with a Waters M6000A solvent pump. The total protein load on the column was found to be generally around 3 mg of protein and the volume applied was usually around 100 ml. The loaded column is washed with 0.1% TFA to remove non-bound sample components until the absorbance at 214 nm drops to baseline, by use of an automated ultraviolet light absorbance detection system to monitor the protein in the column effluents. Elution of the bound proteins is accomplished with a linear gradient of 0-95% acetonitrile in 0.1% TFA (V/V) at a rate of 1% per minute.

As shown by the output plot of the automated ultraviolet light absorbance detection system set forth in FIG. 1, many protein peaks are resolved by the above reverse phase high performance liquid chromatography protocol. Eluate fractions are collected at one minute intervals and then aliquots from each fraction are diluted 1:50 in Click's medium (Altic Assoc., Madison, Wisconsin) containing 10% FCS and then tested for CSF-2 activity using the FDC-P2 assay, as detailed above. As illustrated in FIG. 1, CSF-2 activity at a level of approximately $9.5 \times 10^{-6}$ units of activity per ml of sample was found in a sharp peak of protein which eluted at 48% acetonitrile. This corresponds to a specific activity of about $1 \times 10^6$ units of activity per microgram of protein.

Peak fractions are also analyzed by polyacrylamide gel electrophoresis. In this analysis technique, 20 μl aliquots from the fractions collected during the elution procedure, above, are dried under vacuum after the addition of two ml of 10% SDS to each aliquot. The dried residue is dissolved in 40 μl of non-reducing sample buffer composed of 0.0625M Tris (pH 6.8); 2% SDS (sodium dodecylsulfate (w/u)); 10% glycerol (v/v); and 5%-mercaptoethanol (v/v). The solution is boiled for 3 minutes and then subjected to electrophoresis on a 12% polyacrylamide gel by the method described by Laemmli, 227 *Nature* 680–685 (1970). The gel samples for the individual fraction numbers are silver stained by the method described by Oakley et al., 105 *Anal. Biochem.* 361–364 (1980). If these analysis techniques indicate that the peak fraction is composed of several different proteins, the fraction is subjected to a second reverse phase high-performance liquid chromatography procedure, described in Example 6 below.

EXAMPLE 6

Reverse Phase High-Performance Liquid Chromatography With N-Propanol Elution The fractions containing the peaks of activity obtained from Example 5 are diluted 1:3 with 0.9M acetic acid, 0.2 M pyridine (pH. 4.0) and then applied to a 3.9×300 mm Waters C18 u Bondapak column (Waters Assoc. Milford, Me.) which has been previously equilibrated with the same acetic acid -pyridine buffer. The column is initially washed with the acetic acid-pyridine buffer to remove non-bound components and then the proteins eluted from the column with a 0–95% propanol gradient in the same acetic acid-pyridine buffer. The initial propanol gradient is applied to the column at a rate of 0–20% in 10 minutes and then from 20–84% in 110 minutes at a flow rate of 0.7 ml/min. Applicants have found that CSF-2α activity is eluted under these conditions at 28% propanol. Recovery of CSF-2α activity in this step is in the range of 50 to 200 percent. Essential homogeneity of this material has been confirmed by polyacrylamide gel electrophoresis and silver staining which yielded a single band at approximately 24,500 MW. The specific activity of this homogeneous material was estimated to be $1.1 \times 10^7$ U/μg protein or $2.6 \times 10^{17}$ U/mole. The pI value was found to be approximately 5.50.

EXAMPLE 7

Amino Acid Sequencing

Purified CSF-2 from Example 6 is dried under vacuum to a small volume and then subjected to automated amino terminal Edman degradation using an Applied Biosystems Model 470A protein sequencer. Two sequencing runs are made, the first with approximately 100 pmole of CSF-2α. Applicants found that in the first run, 80% of the sequence could be assigned to a single protein. A second confirming run of approximately 40 pmole of material with lower specific activity is then made. In this run, three sequences were observed concurrently. The first 15 residues of the amino terminal portion of the CSF-2α molecule was found to be composed of the following sequence: Ala-Ser-Ile-Ser-Gly-Arg-Asp-Thr-His-Arg-Lys/Lu-Ghr-Arg-Thr-Leu. Residue number 11 could not be unambiguously differentiated as either Lys or Leu.

As will be apparent to those skilled in the art to which the invention is addressed, the present invention may be carried out by using cell lines and cell lines cloned therefrom, culture media, culture media additives, culture conditions, purification techniques and chromatography columns other than those specifically disclosed above without departing from the spirit or essential characteristics of the invention. The particular materials and processes described above are therefore to be considered in all respects as illustrative and not restrictive, i.e. the scope of the present invention is set forth in the appended claims rather than being limited to the examples of the methods and procedures as set forth in the foregoing description.

The embodiments of the invention in which an exclusive property or privilege is claimed are defined as follows:

1. A process for preparing colony stimulating factor in homogeneous form, comprising:
   (a) passing a solution of crude colony stimulating factor through a reverse phase, high-performance column containing an appropriate ligand covalently bonded to a silica gel whereby the colony stimulating factor is retained by said first column, eluting said first column with an acetonitrile gradient, and pooling fractions exhibiting colony stimulating factor activity; and,
   (b) passing the pooled active fractions eluted from the first column through a second reverse phase, high-performance liquid chromatography column containing an appropriate ligand covalently bonded to a silica gel whereby the colony stimulating factor is retained by the second column, eluting the second column with a buffered N-propanol gradient and pooling fractions exhibiting colony stimulating factor activity.

2. The process of claim 1, wherein the crude colony stimulating factor is rendered acidic prior to being applied to the first column.

3. The process of claim 2, wherein the crude murine colony stimulating factor is rendered acidic with trifluoroacetic acid.

4. The process of claim 1, wherein the buffer in step 18(a) is 0.9 M acetic acid/0.2 M pyridine, pH of approximately 4.0.

* * * * *